US006989477B2

(12) United States Patent
Steidl

(10) Patent No.: US 6,989,477 B2
(45) Date of Patent: Jan. 24, 2006

(54) INBRED CORN LINE 5020

(75) Inventor: Robert P. Steidl, Forrest, IL (US)

(73) Assignee: FFR Cooperative, Lafayette, IN (US)

( * ) Notice: Subject to any disclaimer, the term of this patent is extended or adjusted under 35 U.S.C. 154(b) by 409 days.

(21) Appl. No.: 10/286,467

(22) Filed: Oct. 31, 2002

(65) Prior Publication Data

US 2004/0088768 A1   May 6, 2004

(51) Int. Cl.
*A01H 1/00* (2006.01)
*C07K 14/415* (2006.01)
*C12N 5/14* (2006.01)

(52) U.S. Cl. ............... 800/320.1; 435/70.1; 435/468; 435/412; 435/418; 435/424; 530/370; 536/23.1; 800/260; 800/278; 800/303

(58) Field of Classification Search ............... 435/70.1, 435/468, 412, 418, 424; 530/370; 536/23.1; 800/260, 278, 303, 320.1
See application file for complete search history.

(56) References Cited

U.S. PATENT DOCUMENTS

| | | | |
|---|---|---|---|
| 5,304,717 A | 4/1994 | Miller | |
| 5,304,719 A | 4/1994 | Segebart | |
| 5,367,109 A | 11/1994 | Segebart | |
| 5,523,520 A | 6/1996 | Hunsperger | |
| 6,025,547 A | 2/2000 | Stucker | |
| 6,096,953 A | 8/2000 | Hoffbeck | |
| 6,844,489 B2 * | 1/2005 | Delzer | 800/320.1 |

OTHER PUBLICATIONS

Allard, 1960, Backcross Breeding, In Principles of Plant Breeding, John Wiley & Sons, Inc., pp. 155-156.
Darnell, James, et al., 1990, DNA Replication, Repair and Recombination, In Molecular Cell Biology, $2^{nd}$ Edition, p. 478.
Eshed, et al., 1996, Less-Than-Additive Epistatic Interactions of Quantitative Trait Loci in Tomato, Genetics, vol. 143, pp. 1807-1817.
Kraft, et al., 2000, Linkage Disequilibrium and Fingerprinting in Sugar Beet, Theoretical Applied Genetics, vol. 101, pp. 323-326.
Napoli, Carolyn, et al., 1990, Introduction of a Chimeric Chalcone Synthase Gene into Petunia Results in Reversible Co-Suppression of Homologous Genes in trans, The Plant Cell, vol. 2, pp. 279-289.
Phillips, et al., 1988, Cell/Tissue Culture and In Vitro Manipulation, In Corn and Corn Improvement, American Society of Agronomy Monograph No. 18, $3^{rd}$ edition, p. 358.
Murray, et al., 1988. Restriction fragment length polymorphisms: What are they and how can breeders use them? Proceedings of the $43^{rd}$ Annual Corn and Sorghum Industry Research Conference. 43:72-87.

* cited by examiner

*Primary Examiner*—Phuong T. Bui
(74) *Attorney, Agent, or Firm*—Jondle & Associates P.C.

(57) ABSTRACT

An inbred corn line, designated 5020, is disclosed. The invention relates to the seeds of inbred corn line 5020, to the plants of inbred corn line 5020 and to methods for producing a corn plant, either inbred or hybrid, by crossing the inbred line 5020 with itself or another corn line. The invention further relates to methods for producing a corn plant containing in its genetic material one or more transgenes and to the transgenic plants produced by that method and to methods for producing other inbred corn lines derived from the inbred 5020.

22 Claims, No Drawings

INBRED CORN LINE 5020

BACKGROUND OF THE INVENTION

The present invention relates to a new and distinctive corn inbred line, designated 5020. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior corn inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new corn inbred line.

The development of commercial corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Hybrid corn seed is typically produced by a male sterility system incorporating manual or mechanical detasseling. Alternate strips of two corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male), and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in corn plants, since only the female provides cytoplasm to the fertilized seed. CMS plants are fertilized with pollen from another inbred that is not male-sterile. Pollen from the second inbred may or may not contribute genes that make the hybrid plants male-fertile. Seed from detasseled fertile corn and CMS produced seed of the same hybrid can be blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. These and all patents referred to are incorporated by reference. In addition to these methods, Albertsen et al., U.S. Pat. No. 5,432,068 have developed a system of nuclear male sterility which includes: identifying a gene which is critical to male fertility, silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see, Fabinjanski, et al. EPO 89/3010153.8 publication no. 329, 308 and PCT application PCT/CA90/00037 published as WO 90/08828).

Another version useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, G. R., U.S. Pat. No. 4,936,904). Application of the gametocide, timing of the application and genotype specifically often limit the usefulness of the approach.

Corn is an important and valuable field crop. Thus, a continuing goal of plant breeders is to develop stable, high yielding corn hybrids that are agronomically sound. The reasons for this goal are obviously to maximize the amount of grain produced on the land used and to supply food for both animals and humans. To accomplish this goal, the corn breeder must select and develop corn plants that have the traits that result in superior parental lines for producing hybrids.

SUMMARY OF THE INVENTION

According to the invention, there is provided a novel inbred corn line, designated 5020. This invention thus relates to the seeds of inbred corn line 5020, to the plants of inbred corn line 5020 and to methods for producing a corn plant produced by crossing the inbred line 5020 with itself or another corn line, and to methods for producing a corn plant containing in its genetic material one or more transgenes and to the transgenic corn plants produced by that method. This invention also relates to methods for producing other inbred corn lines derived from inbred corn line 5020 and to the inbred corn lines derived by the use of those methods. This invention further relates to hybrid corn seeds and plants produced by crossing the inbred line 5020 with another corn line.

The inbred corn plant of the invention may further comprise, or have, a cytoplasmic factor that is capable of conferring male sterility. Parts of the corn plant of the present invention are also provided, such as e.g., pollen obtained from an inbred plant and an ovule of the inbred plant.

In another aspect, the present invention provides regenerable cells for use in tissue culture or inbred corn plant 5020. The tissue culture will preferably be capable of regenerating plants having the physiological and morphological characteristics of the foregoing inbred corn plant, and of regenerating plants having substantially the same genotype as the foregoing inbred corn plant. Preferably, the regenerable cells in such tissue cultures will be embryos, protoplasts, meristematic cells, callus, pollen, leaves, anthers, roots, root tips, silk, flowers, kernels, ears, cobs, husks or stalks. Still further, the present invention provides corn plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Predicted RM. This trait for a hybrid, predicted relative maturity (RM), is based on the harvest moisture of the grain. The relative maturity rating is based on a known set of checks and utilizes conventional maturity systems such as the Minnesota Relative Maturity Rating System.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Yield (Bushels/Acre). The yield in bushels/acre is the actual yield of the grain at harvest adjusted to 15.5% moisture.

Moisture. The moisture is the actual percentage moisture of the grain at harvest.

GDU Silk. The GDU silk (=heat unit silk) is the number of growing degree units (GDU) or heat units required for an inbred line or hybrid to reach silk emergence from the time of planting. Growing degree units are calculated by the Barger Method, where the heat units for a 24-hour period are:

$$GDU = \frac{(Max.+Min)}{2} - 50.$$

The highest maximum used is 86° F. and the lowest minimum used is 50° F. For each hybrid, it takes a certain number of GDUs to reach various stages of plant development. GDUs are a way of measuring plant maturity.

Stalk Lodging. This is the percentage of plants that stalk lodge, i.e., stalk breakage, as measured by either natural lodging or pushing the stalks determining the percentage of plants that break off below the ear. This is a relative rating of a hybrid to other hybrids for standability.

Root Lodging. The root lodging is the percentage of plants that root lodge; i.e., those that lean from the vertical axis at an approximate 30° angle or greater would be counted as root lodged.

Plant Height. This is a measure of the height of the hybrid from the ground to the tip of the tassel, and is measured in centimeters.

Ear Height. The ear height is a measure from the ground to the ear node attachment, and is measured in centimeters.

Dropped Ears. This is a measure of the number of dropped ears per plot, and represents the percentage of plants that dropped an ear prior to harvest.

Allele. The allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

DETAILED DESCRIPTION OF THE INVENTION

Inbred corn line 5020 is a yellow dent corn with superior characteristics, and provides an excellent parental line in crosses for producing first generation ($F_1$) hybrid corn.

Yield, stalk quality, root quality, disease tolerance, late plant greenness, late plant intactness, ear retention, pollen shedding ability, silking ability and corn borer tolerance were the criteria used to determine the rows from which ears were selected.

Inbred corn line 5020 has the following morphologic and other characteristics (based primarily on data collected at West Lafayette, Indiana).

VARIETY DESCRIPTION INFORMATION

TYPE: Dent
REGION WHERE DEVELOPED: Central Corn Belt
MATURITY:
Heat units to silking: 1423 GDD $$Heat\ Units: = \frac{[Max.\ Temp.(\leq 86°\ F.) + Min.\ Temp.(\geq 50°\ F.)]}{2} - 50$$

PLANT:
Plant Height (to tassel tip): 192.4 cm
Ear Height (to base of top ear): 76 cm
Average Length of Top Ear Internode: 14.2 cm
Average number of Tillers: 0
Average Number of Ears per Stalk: 1.6
Cytoplasm type: normal
 LEAF:
Width of Ear Node Leaf: 9.4 cm
Length of Ear Node Leaf: 72.2 cm
Color: Green—Munsell Code 5GY 4/6
Leaf Angle: 26.8°
Leaf Sheath Pubescence (Rate on scale from 1=none to 9=like peach fuzz): 2
Marginal Waves (Rate on scale from 1=none to 9=many): 4
Longitudinal Creases (Rate on scale from 1=none to 9=many): 6

TASSEL:
Number of Lateral Branches: 3.4
Branch Angle from Central Spike: 33.6°
Pollen Shed (Rate on scale from 0=male sterile to 9=heavy shed): 5–6
Anther Color: Munsell Code 5Y 8/6
Glume Color: Munsell Code 2.5GY 8/8
  EAR: (Husked ear data except when stated otherwise)
Silk Color: Munsell Code 2.5GY 8/10
Fresh Husk Color: Munsell Code 2.5GY 8/8
Dry Husk Color: Munsell Code 2.5Y 8/4
Position of Ear: Erect
Husk Extension: 5.2 cm
Ear Length: 14.5 cm
Ear Diameter at mid-point: 3.5 cm
Ear Weight: 78.1 g
Number of Kernel Rows: 13.8
Kernel Rows (alignment): Regular, spiral
Shank Length: 9.4 cm
  KERNEL: (Dried)
Kernel Length: 8.9 mm
Kernel Width: 7.0 mm
Kernel Thickness: 4.5 mm
Round Kernels (Shape Grade): 22%
Aleurone Color: Transparent
Hard Endosperm Color: Yellow-orange
Endosperm Type: Normal Starch
Weight per 100 kernels: 18.3 gm
  COB:
Cob Diameter at Mid-Point: 2.3 cm
Cob Color: Red
  DISEASE RESISTANCE:

| Rating [1 = (most susceptible) through 9 = (most resistant)] | |
|---|---|
| 7 | Gray Leaf Spot (*Cercospora zeae-maydis*) |

This invention is also directed to methods for producing a corn plant by crossing a first parent corn plant with a second parent corn plant, wherein the first or second corn plant is the inbred corn plant from the line 5020. Further, both first and second parent corn plants may be from the inbred line 5020. Therefore, any methods using the inbred corn line 5020 are part of this invention: selfing, backcrosses, hybrid breeding, and crosses to populations. Any plants produced using inbred corn line 5020 as a parent are within the scope of this invention. Advantageously, the inbred corn line is used in crosses with other corn varieties to produce first generation ($F_1$) corn hybrid seed and plants with superior characteristics.

5020 is similar to TR5758, however, there are numerous differences including: 5020 is red cobbed whereas TR5758 is white cobbed. Additionally 5020 flowers approximately 30 GDD's later than TR5758 and is approximately 35 cm taller.

Some of the criteria used to select ears in various generations include: yield, stalk quality, root quality, disease tolerance, late plant greenness, late season plant intactness, ear retention, pollen shedding ability, silking ability, and corn borer tolerance. During the development of the line, crosses were made to inbred testers for the purpose of estimating the line's general and specific combining ability, and evaluations were run by the West Lafayette, Ind. Research Station. The inbred was evaluated further as a line and in numerous crosses by other research stations across the Corn Belt. The inbred has proven to have fair combining ability in hybrid combinations.

The inbred has shown uniformity and stability within the limits of environmental influence for the traits. It has been self-pollinated and ear-rowed a sufficient number of generations, with careful attention to uniformity of plant type to ensure homozygosity and phenotypic stability necessary to use in commercial production. The line has been increased both by hand and sibbed in isolated fields with continued observations for uniformity. No variant traits have been observed or are expected in 5020.

FURTHER EMBODIMENTS OF THE INVENTION

This invention also is directed to methods for producing a corn plant by crossing a first parent corn plant with a second parent corn plant wherein either the first or second parent corn plant is an inbred corn plant of the line 5020. Further, both first and second parent corn plants can come from the inbred corn line 5020. Still further, this invention also is directed to methods for producing an inbred corn line 5020 -derived corn plant by crossing inbred corn line 5020 with a second corn plant and growing the progeny seed, and repeating the crossing and growing steps with the inbred corn line 5020-derived plant from 0 to 7 times. Thus, any such methods using the inbred corn line 5020 are part of this invention: selfing, backcrosses, hybrid production, crosses to populations, and the like. All plants produced using inbred corn line 5020 as a parent are within the scope of this invention, including plants derived from inbred corn line 5020. Advantageously, the inbred corn line is used in crosses with other, different, corn inbreds to produce first generation ($F_1$) corn hybrid seeds and plants with superior characteristics.

It should be understood that the inbred can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which corn plants can be regenerated, plant calli, plant clumps and plant cells that are intact in plants or parts of plants, such as embryos, pollen, ovules, flowers, kernels, ears, cobs, leaves, husks, stalks, roots, root tips, anthers, silk and the like.

Duncan, et al., *Planta* 165:322–332 (1985) reflects that 97% of the plants cultured that produced callus were capable of plant regeneration. Subsequent experiments with both inbreds and hybrids produced 91% regenerable callus that produced plants. In a further study in 1988, Songstad, et al., *Plant Cell Reports* 7:262–265 (1988), reports several media addations that enhance regenerability of callus of two inbred lines. Other published reports also indicated that "nontraditional" tissues are capable of producing somatic embryogenesis and plant regeneration. K. P. Rao et al., *Maize Genetics Cooperation Newsletter,* 60:64–65 (1986), refers to somatic embryogenesis from glume callus cultures and B. V. Conger, et al., *Plant Cell Reports,* 6:345–347 (1987) indicates somatic embryogenesis from the tissue cultures of corn leaf segments. Thus, it is clear from the literature that the state of the art is such that these methods of obtaining plants are, and were, "conventional" in the sense that they are routinely used and have a very high rate of success.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottesville, Va. 367–372, (1982))

and in Duncan et al., "The Production of Callus Capable of Plant Regeneration from Immature Embryos of Numerous Zea Mays Genotypes," 165 *Planta* 322:332 (1985). Thus, another aspect of this invention is to provide cells which upon growth and differentiation produce corn plants having the physiological and morphological characteristics of inbred corn line 5020.

The utility of inbred corn line 5020 also extends to crosses with other species. Commonly, suitable species will be of the family Graminaceae, and especially of the genera *Zea, Tripsacum, Croix, Schlerachne, Polytoca, Chionachne,* and *Trilobachne,* of the tribe Maydeae. Potentially suitable for crosses with 5020 may be the various varieties of grain sorghum, *Sorghum bicolor* (L.) Moench.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed inbred line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed corn plants, using transformation methods as described below to incorporate transgenes into the genetic material of the corn plant(s).

Expression Vectors for Corn Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.,* 80:4803 (1983). Another commonly used selectable marker gene is the hygromycin phosphotransferase gene which confers resistance to the antibiotic hygromycin. Vanden Elzen et al., *Plant Mol. Biol.,* 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.,* 210:86 (1987), Svab et al., *Plant Mol. Biol.* 14:197 (1990<Hille et al., *Plant Mol. Biol.* 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) and Stalker et al., *Science* 242:419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol, acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984). Another approach to the identification of relatively rare transformation events has been use of a gene that encodes a dominant constitutive regulator of the *Zea mays* anthocyanin pigmentation pathway. Ludwig et al., *Science* 247:449 (1990).

Recently, in vivo methods for visualizing GUS activity that do not require destruction of plant tissue have been made available. Molecular Probes publication 2908, Imagene Green™, p. 1–4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in corn. Optionally, the inducible promoter is operably linked to a nucleotide sequence encoding a signal sequence which is operably linked to a gene for expression in corn. With an inducible promoter the rate of transcription increases in response to an inducing agent.

Any inducible promoter can be used in the instant invention. See Ward et al., *Plant Mol. Biol.* 22:361–366 (1993). Exemplary inducible promoters include, but are not limited to, that from the ACEI system which responds to copper (Meft et al., *PNAS* 90:4567–4571 (1993)); In2 gene from maize which responds to benzenesulfonamide herbicide safeners (Hershey et al., *Mol. Gen Genetics* 227:229–237 (1991) and Gatz et al., *Mol. Gen. Genetics* 243:32–38 (1994)) or Tet repressor from Tn10 (Gatz et al., *Mol. Gen. Genetics* 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in corn or the constitutive promoter is operably linked to a nucleotide sequence encoding a signal sequence which is operably linked to a gene for expression in corn.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3): 291–300 (1992)).

The ALS promoter, Xba1/Ncol fragment 5' to the *Brassica napus* ALS3 structural gene (or a nucleotide sequence similarity to said Xba1/Ncol fragment), represents a particularly useful constitutive promoter. See PCT application WO96/30530.

C. Tissue-Specific or Tissue-Preferred Promoters

A tissue-specific promoter is operably linked to a gene for expression in corn. Optionally, the tissue-specific promoter is operably linked to a nucleotide sequence encoding a signal sequence which is operably linked to a gene for expression in corn. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476–482 (1983) and Sengupta-Gopalan et al., *Proc. Natl Acad. Sci. U.S.A.* 82:3320–3324 (1985)); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217: 240–245 (1989)); a pollen-specific promoter such as that from Zm13 (Guerrero et al., *Mol. Gen. Genetics* 244: 161–168 (1993)) or a microspore-preferred promoter such as that from apg (Twell et al., *Sex. Plant Reprod.* 6:217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3–17 (1987), Lerner et al., *Plant Physiol.* 91:124–129 (1989), Fontes et al., *Plant Cell* 3:483–496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499–509 (1984), Steifel, et al., Expression of a maize cell wall hydroxyproline-rich glycoprotein gene in early leaf and root vascular differentiation, *Plant Cell* 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is corn. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant inbred line can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); Mindrinos et. al., *Cell* 78:1089 (1994) (Arabidopsis RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclose by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in Diploptera puntata). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A development-arrestive protein produced in nature by a plant. For example, Logemann et al., *Bioi/Technology* 10:305 (1992), have shown that transgenic plants expressing the barley ribosome-inactivating gene have an increased resistance to fungal disease.

2. Genes That Confer Resistance to a Herbicide, For Example:

A. A herbicide that inhibits the growing point or meristem, such as an imidazalinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2 and Acc1-S3 genes described by Marshall et al., *Theor. Appl. Genet.* 83:435 (1992).

C. A herbicide that inhibits photosynthesis, such as a triazine (psbA and gs+ genes) and a benzonitrile (nitrilase gene). Przibilla et al., *Plant Cell* 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes That Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased phytate content 1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

Methods for Corn Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89–119.

A. Agrobacterium-mediated Transformation

One method for introducing an expression vector into plants is based on the natural transformation system of Agrobacterium. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of Agrobacterium vector systems and methods for Agrobacterium-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer

Despite the fact the host range for Agrobacterium-mediated transformation is broad, some major cereal crop species and gymnosperms have generally been recalcitrant to this mode of gene transfer, even though some success has recently been achieved in rice and corn. Hiei et al., *The Plant Journal* 6:271–282 (1994) and U.S. Pat. No. 5,591,616 issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of micropojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559–563 (1988), Sanford, J. C., *Physiol Plant* 7:206 (1990), Klein et al., *Biotechnology* 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-omithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495–1505 (1992) and Spencer et al., *Plant Mol. Biol.* 24:51–61 (1994).

Following transformation of corn target tissues, expression of the above-described selectable marker genes allows for preferential selection of transformed cells, tissues and/or plants, using regeneration and selection methods now well known in the art.

The foregoing methods for transformation would typically be used for producing a transgenic inbred line. The transgenic inbred line could then be crossed, with another (non-transformed or transformed) inbred line, in order to produce a new transgenic inbred line. Alternatively, a genetic trait which has been engineered into a particular corn line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term inbred corn plant is used in the context of the present invention, this also includes any single gene conversions of that inbred. The term single gene converted plant as used herein refers to those corn plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental corn plants for that inbred. The parental corn plant which contributes the gene for the desired characteristic is termed the nonrecurrent or donor parent. This terminology refers to the fact that the nonrecurrent parent is used one time in the backcross protocol and therefore does not recur. The parental corn plant to which the gene or genes from the nonrecurrent parent are transferred is known as the recurrent parent as it is used for several rounds in the backcrossing protocol (Poehiman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

INDUSTRIAL APPLICABILITY

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs and poultry.

Industrial uses of corn include production of ethanol, corn starch in the wet-milling industry and corn flour in the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds and other mining applications.

Plant parts other than the grain of corn are also used in industry, for example: stalks and husks are made into paper and wallboard and cobs are used for fuel and to make charcoal.

The seed of inbred corn line 5020, the plant produced from the inbred seed, the hybrid corn plant produced from the crossing of the inbred, hybrid seed, and various parts of the hybrid corn plant and transgenic versions of the foregoing, can be utilized for human food, livestock feed, and as a raw material in industry.

TABLES

In the tables that follow, the traits and characteristics of inbred corn line 5020 are given in hybrid combination. The data collected on inbred corn line 5020 is presented for the key characteristics and traits. The tables present yield test information about 5020. 5020 was tested in hybrid combination at numerous locations, with two or three replications per location. Information about these hybrids, as compared to check hybrids, is presented.

The first column gives the hybrid containing 5020 and check hybrids. Column 2 gives the mean yield of the hybrids across all locations. Columns 3 and 4 give the mean for the percentage moisture (% Mst) for the hybrids across all locations and the yield/moisture ratio. Columns 5 and 6 reflect the mean of percentage of plants with root lodging (% Root) and stalk lodging (% Stalk) across all locations. Columns 7 gives test weights measured in pounds per bushel.

TABLE 1

| Hybrid | Yield | % Mst | Y/M | % Stalk | % Root | Tst Wt |
|---|---|---|---|---|---|---|
| 2001 Data 10 Locations | | | | | | |
| SGI890 × 5020 | 188.7 | 18.3 | 10.4 | 4.1 | 3.1 | 58.9 |
| LH198 × 5020 | 183.9 | 18.4 | 10.0 | 5.8 | 6.6 | 58.7 |
| TR8284 × 5020 | 183.2 | 18.3 | 10.0 | 6.2 | 6.3 | 58.1 |
| HC33 × 5020 | 180.0 | 17.7 | 10.2 | 7.8 | 2.6 | 58.8 |
| LH198 × LH273 | 183.9 | 17.8 | 10.4 | 7.5 | 4.4 | 57.9 |
| SGI822 × SGI885 | 163.8 | 17.9 | 9.1 | 8.2 | 2.0 | 58.3 |
| LH198 × SGI851 | 193.4 | 18.9 | 10.3 | 5.4 | 8.9 | 58.2 |
| Pioneer 35P12 | 176.0 | 18.1 | 9.7 | 9.2 | 4.4 | 58.0 |
| Pioneer 34G81 | 179.7 | 18.1 | 10.0 | 6.4 | 11.6 | 58.3 |
| Pioneer 34B23 | 183.1 | 18.5 | 9.9 | 8.3 | 5.2 | 58.6 |
| 2000 Data 11 Locations | | | | | | |
| LH198 × 5020 | 176.2 | 18.5 | 9.5 | 10.1 | 4.1 | 54.9 |
| LH198 × LH273 | 181.5 | 18.8 | 9.7 | 7.3 | 4.2 | 53.1 |
| LH198 × LH185 | 162.7 | 19.1 | 8.5 | 9.4 | 7.3 | 50.9 |
| SG1822 × SGI885 | 156.1 | 17.5 | 8.9 | 11.1 | 0.9 | 53.4 |
| Pioneer 35N05 | 151.7 | 18.9 | 8.0 | 14.6 | 3.6 | 58.6 |
| Pioneer 34G81 | 175.5 | 17.7 | 9.9 | 5.9 | 7.7 | 59.3 |
| Pioneer 33G26 | 175.0 | 21.0 | 8.3 | 4.8 | 2.7 | 56.3 |

TABLE 1-continued

| Hybrid | Yield | % Mst | Y/M | % Stalk | % Root | Tst Wt |
|---|---|---|---|---|---|---|
| 1999 Data 6 Locations | | | | | | |
| LH198 × 5020 | 185.7 | 15.2 | 12.2 | 0.9 | 23.3 | |
| LH198 × LH185 | 186.7 | 15.7 | 11.9 | 0.5 | 23.3 | |
| Pioneer 3489 | 184.5 | 16.0 | 11.5 | 1.8 | 22.2 | |

DEPOSIT INFORMATION

A deposit of the FFR Cooperative proprietary inbred corn line 5020 disclosed above and recited in the appended claims has been made with the American Type Culture Collection (ATCC), 10801 University Boulevard, Manassas, Va. 20110. The date of deposit was Jul. 15, 2005. The deposit of 2,500 seeds was taken from the same deposit maintained by FFR Cooperative since prior to the filing date of this application. All restrictions upon the deposit have been removed, and the deposit is intended to meet all of the requirements of 37 C.F.R. 1.801–1.809. The ATCC accession number is PTA-6868. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding. However, it will be obvious that certain changes and modifications such as single gene modifications and mutations, somoclonal variants, variant individuals selected from large populations of the plants of the instant inbred and the like may be practiced within the scope of the invention, as limited only by the scope of the appended claims.

What is claimed is:

1. Seed of corn inbred line designated 5020, representative seed of said line having been deposited under ATCC Accession No. PTA-6868.

2. A corn plant, or a part thereof, produced by growing the seed of claim 1.

3. Pollen of the plant of claim 2.

4. An ovule of the plant of claim 2.

5. A corn plant, or a part thereof, having all of the physiological and morphological characteristics of the corn plant of claim 2.

6. A tissue culture of regenerable cells prepared from the corn plant of claim 2.

7. The tissue culture according to claim 6, wherein the cells or protoplasts of said cells are produced from a tissue selected from the group consisting of leaves, pollen, embryos, roots, root tips, anthers, silks, flowers, kernels, ears, cobs, husks, and stalks.

8. A corn plant regenerated from the tissue culture of claim 6, wherein the regenerated plant has all the morphological and physiological characteristics of inbred plant 5020, wherein a sample of seed of said inbred corn plant has been deposited under ATCC Accession No. PTA-6868.

9. A corn plant with all of the physiological and morphological characteristics of corn inbred 5020, wherein said corn plant is produced by the tissue culture of claim 7.

10. A method for producing an F1 hybrid corn seed comprising crossing a first inbred parent corn plant with a second inbred parent corn plant and harvesting the resultant hybrid corn seed, wherein said first inbred parent corn plant or said second inbred parent corn plant is the corn plant of claim 2.

11. A method of producing a transgenic corn plant comprising transforming the corn plant of claim 2 with a transgene that confers a characteristic selected from the group consisting of herbicide resistance, insect resistance, resistance to bacterial disease, resistance to fungal disease, resistance to viral disease, and male sterility.

12. A transgenic corn plant produced by the method of claim 11.

13. A method of producing an herbicide resistant corn plant comprising transforming the corn plant of claim 2 with a transgene that confers herbicide resistance.

14. An herbicide resistant corn plant produced by the method of claim 13.

15. A method of producing an insect resistant corn plant comprising transforming the corn plant of claim 2 with a transgene that confers insect resistance.

16. An insect resistant corn plant produced by the method of claim 15.

17. A method of producing a disease resistant corn plant comprising transforming the corn plant of claim 2 with a transgene that confers disease resistance.

18. A disease resistant corn plant produced by the method of claim 17.

19. A method of producing a corn plant with decreased phytate content comprising transforming the corn plant of claim 2 with a transgene encoding phytase.

20. A corn plant with decreased phytate content, produced by the method of claim 19.

21. A method of producing a corn plant with modified fatty acid or carbohydrate metabolism comprising transforming the corn plant of claim 2 with one or more transgenes expressing a protein selected from the group consisting of fructosyltransferase, levansucrase, alpha-amylase, invertase and starch branching enzyme, or encoding an antisense of stearyl-ACP desaturase.

22. A corn plant produced by the method of claim 21.

* * * * *